United States Patent [19]

Shuber

[11] Patent Number: 5,571,676

[45] Date of Patent: Nov. 5, 1996

[54] METHOD FOR MISMATCH-DIRECTED IN VITRO DNA SEQUENCING

[75] Inventor: Anthony P. Shuber, Milford, Mass.

[73] Assignee: IG Laboratories, Inc., Framingham, Mass.

[21] Appl. No.: 487,986

[22] Filed: Jun. 7, 1995

[51] Int. Cl.⁶ .............................. C12Q 1/68; C12Q 1/70; C12P 19/34; C07H 21/04

[52] U.S. Cl. .................... 435/6; 435/91.2; 435/5; 536/24.3; 536/24.31; 536/24.33

[58] Field of Search .................... 435/6, 91.2, 5; 536/24.3–.33

[56] References Cited

U.S. PATENT DOCUMENTS 5,459,039  10/1995  Modrich et al. ..................... 435/6

OTHER PUBLICATIONS

Lu and Hsu, *Genomics* 14: 249–255 1992.
Su et al. *Genome* 31: 104–111 1992.
Landegren U et al., *Science*, 241:1077–1080, 1988.
Mashal et al., *Nature Genetics*, 9:177, 1995.
Maxam AM et al., *Methods Enzymol.*, 65:499–560, 1980.
Mayall et al., *J. Med. Genet.*, 27:658, 1990.
Meyers RM et al., *Nature*, 313:495–498, 1985.
Newton CR et al., *Nuc Acids Res.*, 17:2503–2516, 1989.
Orita M et al., *Proc. Natl. Acad. Sci. USA*, 86:2766–2770, 1989.
Pease et al., *Proc. Natl. Acad. Sci. USA*, 91:5022, 1994.
Richards et al., *Human Mol. Gen.*, 2:159, 1993.
Rommens et al., *Am. J. Genet.*, 46:395–396, 1990.
Saleeba et al., *Meth. Enzymol.*, 217:288, 1993.
Sancar, *Science*, 266:1954, 1994.
Shuber et al., *Human Molecular Genetics*, 2:153–158, 1993.
Sokolov, BP, *Nucl. Acids Res.*, 18:3671, 1989.
Southern, E. M., *J. Mol. Biol.*, 98:503–517, 1975.
Su et al., *Proc. Natl. Acad. Sci. USA*, 83:5057, 1986.
Thompson and Thompson, *Genetics in Medicine*, 5th Ed.
Tsai–Wu et al., *J. Bacteriol.*, 178:1902, 1991.
Wallace RB et al., *Nucl. Acids Res.*, 9:879–895, 1981.
Yeh et al., *J. Biol. Chem.*, 266:6480, 1991.
Youil et al., *Proc. Natl.Acad. Sci. USA*, 92:87, 1995.
Aboussekhra et al., *Cell* 80:859, 1995.
Chang et al., *Nuc. Acids Res.* 19:4761, 1991.
Chehab et al., *Nature*, 329:293–294, 1987.
Cleaver, *Cell*, 76:1–4, 1994.
Cohen LB et al., *Nature*, 334:119–121, 1988.
Cotton RGH et al., *Proc. Natl. Acad. Sci.*, 85:4397–4401, 1988.
Grilley et al., *J. Biol. Chem.*, 264:1000, 1989.
Haliassos et al., *Nucleic Acids Research*, 17:3606, 1989.
Huang et al., *Proc. Natl. Acad. Sci. USA*, 91:12213, 1994.
Keen J. et al., *Trends Genet.*, 7:5, 1991.
Kosak et al., *Eur. J. Biochem.*, 194:779, 1990.

*Primary Examiner*—Stephanie W. Zitomer
*Assistant Examiner*—Dianne Rees
*Attorney, Agent, or Firm*—Darby & Darby, P.C.

[57] ABSTRACT

The present invention relates to methods for identifying the location, and determining the sequence of specific genetic alterations present in a gene of interest.

32 Claims, No Drawings

METHOD FOR MISMATCH-DIRECTED IN VITRO DNA SEQUENCING

FIELD OF THE INVENTION

This invention pertains to high-throughput methodology that directly identifies previously unidentified sequence alterations in DNA, including specific disease-causing DNA sequences in mammals. The methods of the present invention can be used to identify genetic polymorphisms, to determine the molecular basis for genetic diseases, and to provide carrier and prenatal diagnosis for genetic counseling.

BACKGROUND OF THE INVENTION

The ability to detect alterations in DNA sequences (e.g. mutations and polymorphisms) is central to the diagnosis of genetic diseases and to the identification of clinically significant variants of disease-causing microorganisms. One method for the molecular analysis of genetic variation involves the detection of restriction fragment length polymorphisms (RFLPs) using the Southern blotting technique (Southern, E. M., J. Mol. Biol., 98:503–517, 1975. Since this approach is relatively cumbersome, new methods have been developed, some of which are based on the polymerase chain reaction (PCR). These include: RFLP analysis using PCR (Chehab et al., Nature, 329:293–294, 1987; Rommens et al., Am. J. Hum. Genet., 46:395–396, 1990), the creation of artificial RFLPs using primer-specified restriction-site modification (Haliassos et al., Nucleic Acids Research, 17:3606, 1989), allele-specific amplification (ASA) (Newton CR et al., Nuc. Acids Res., 17:2503–2516, 1989), oligonucleotide ligation assay (OLA) (Landergren U et al., Science 241:1077–1080, 1988), primer extension (Sokolov BP, Nucl. Acids Res., 18:3671, 1989), artificial introduction of restriction sites (AIRS) (Cohen LB et al., Nature 334:119–121, 1988), allele-specific oligonucleotide hybridization (ASO) (Wallace RB et al., Nucl. Acids Res., 9:879–895, 1981) and their variants. Together with robotics, these techniques for direct mutation and analysis have helped in reducing cost and increasing throughput when only a limited number of mutations need to be analyzed for efficient diagnostic analysis.

These methods are, however, limited in their applicability to complex mutational analysis. For example, in cystic fibrosis, a recessive disorder affecting 1 in 2000–2500 live births in the United States, more than 225 presumed disease-causing mutations have been identified. Furthermore, multiple mutations may be present in a single affected individual, and may be spaced within a few base pairs of each other. These phenomena present unique difficulties in designing clinical screening methods that can accommodate large numbers of sample DNAs.

Co-pending U.S. patent application Ser. No. 07/957,205 of Shuber et al. and Shuber et al., Human Molecular Genetics, 2:153–158, 1993, disclose a method that allows the simultaneous hybridization of multiple oligonucleotide probes to a single target DNA sample. By including in the hybridization reaction an agent that eliminates the disparities in melting temperatures of hybrids formed between synthetic oligonucleotides and target DNA, it is possible in a single test to screen a DNA sample for the presence of different mutations. Typically, more than 100 ASOs can be pooled and hybridized to target DNA; in a second step, ASOs from a pool giving a positive result are individually hybridized to the same DNA. Co-pending U.S. patent application Ser. No. 08/281,940 discloses a method for multiple allele-specific disease analysis in which multiple ASOs are first hybridized to a target DNA, followed by elution and sequencing of ASOs that hybridize. This method allows the identification of a mutation without the need for many individual hybridizations involving single ASOs and requires prior knowledge of relevant mutations.

To achieve adequate detection frequencies for rare mutations using the above methods, however, large numbers of mutations must be screened. To identify previously unknown mutations within a gene, other methodologies have been developed, including: single-strand conformational polymorphisms (SSCP) (Orita M et al., Proc. Natl. Acad. Sci. USA 86:2766–2770, 1989), denaturing gradient gel electrophoresis (DGGE) (Meyers RM et al., Nature 313:495–498, 1985), heteroduplex analysis (HET) (Keen j. et al., Trends Genet. 7:5, 1991), chemical cleavage analysis (CCM) (Cotton RGH et al., Proc. Natl. Acad. Sci., 85:4397–4401, 1988), and complete sequencing of the target sample (Maxam AM et al., Methods Enzymol. 65:499–560, 1980, Sanger F. et al., Proc. Natl. Acad. Sci. USA 74:5463–5467, 1977). All of these procedures however, with the exception of direct sequencing, are merely screening methodologies. That is, they merely indicate that a mutation exists, but cannot specify the exact sequence and location of the mutation. Therefore, identification of the mutation ultimately requires complete sequencing of the DNA sample. For this reason, these methods are incompatible with high-throughput and low-cost routine diagnostic methods.

Thus, there is a need in the art for a relatively low cost method that allows the efficient analysis of large numbers of DNA samples for the presence of previously unidentified mutations or sequence alterations.

SUMMARY OF THE INVENTION

The present invention encompasses high-throughput methods for identifying one or more genetic alterations in a target DNA sequence present in a DNA sample. The method is carried out by the steps of:

a) cleaving one DNA strand in the target DNA sequence to form a single-stranded gap across the site of the alteration;

b) determining the nucleotide sequence across the gap; and c) comparing the nucleotide sequence determined in d) with a predetermined cognate wild-type sequence to identify the alteration.

In practicing the present invention, the target DNA is hybridized under stringent conditions with a second DNA sample not containing the alteration. The hybrids that form contain mismatch regions, which are recognized and endonucleolytically cleaved on one or both sides of the mismatch region by mismatch recognition protein-based systems. When a single endonucleolytic cleavage occurs on only one side of the mismatch region, one or more exonucleases are used to form the single-stranded gap. When endonucleolytic cleavage occurs on both sides of the mismatch region, the single-stranded fragment is released by the action of a helicase to form the single-stranded gap. Determination of the sequence across the gap is achieved in a single step by an enzymatic DNA sequencing reaction using dideoxynucleotides and DNA polymerase I, DNA polymerase III, T4 DNA polymerase, or T7 DNA polymerase.

Typically, the first DNA sample comprises genomic DNA from a patient suffering from a genetic disease whose genome does not contain any of the known mutations that cause that disease, and the target DNA sequence comprises a known disease-causing gene. The genetic alterations identified by these methods include additions, deletions, or substitutions of one or more nucleotides. Mismatch recognition, cleavage, and excision systems useful in practicing the invention include without limitation mismatch repair proteins, nucleotide excision repair proteins, chemical modification of mismatched bases followed by excision repair proteins, and combinations thereof, with or without supplementation with exonucleases as required.

The present invention finds application in high-throughput methods for multiplex identification of new disease-causing mutations, in which a multiplicity of patients' DNAs are subjected to hybridization, formation of gapped heteroduplexes, sequencing, and sequence comparison steps as above.

DETAILED DESCRIPTION OF THE INVENTION

All patent applications, patents, and literature references cited in this specification are hereby incorporated by reference in their entirety. In case of conflict, the present description, including definitions, will control.

The present invention encompasses high-throughput methods for identifying specific DNA sequences in DNA isolated from a patient. As used herein, the term high-throughput refers to a system for rapidly assaying large numbers of DNA samples at the same time. The methods are applicable when one or more genes or genetic loci are targets of interest. The specific sequences typically contain one or more sequence alterations relative to wild-type DNA, including additions, deletions, or substitutions of one or more nucleotides.

In practicing the methods of the present invention, the target DNA sequence is hybridized with a sample of DNA (or a pool of DNA samples) containing one or more wild-type versions of the target gene. The methods of the present invention take advantage of the physico-chemical properties of DNA hybrids between almost-identical (but not completely identical) DNA strands (i.e., heteroduplexes). When a sequence alteration is present, the heteroduplexes contain a mismatch region that is embedded in an otherwise perfectly matched hybrid. According to the present invention, mismatch regions are formed under controlled conditions and are chemically and/or enzymatically modified; the sequences adjacent to, and including, the mismatch are then determined. Depending upon the mismatch recognition method used, the mismatch region may comprise any number of bases, preferably from 1 to about 1000 bases. The methods of the invention can be employed to identify specific disease-causing mutations in individual patients (when the gene or genes responsible for the disease are known) and for positional cloning to identify new disease-causing genes.

In a preferred embodiment, the specific DNA sequence comprises a portion of a particular gene or genetic locus in the patient's genomic DNA known to be involved in a pathological condition or syndrome. Non-limiting examples of genetic syndromes include cystic fibrosis, sickle-cell anemia, thalassemias, Gaucher's disease, adenosine deaminase deficiency, alpha1-antitrypsin deficiency, Duchenne muscular dystrophy, familial hypercholesterolemia, fragile X syndrome, glucose-6-phosphate dehydrogenase deficiency, hemophilia A, Huntington disease, myotonic dystrophy, neurofibromatosis type 1, osteogenesis imperfecta, phenylketonuria, retinoblastoma, Tay-Sachs disease, and Wilms tumor (Thompson and Thompson, Genetics in Medicine, 5th Ed.).

In another embodiment, the specific DNA sequence comprises part of a particular gene or genetic locus that may not be known to be linked to a particular disease, but in which polymorphism is known or suspected. For example, obesity may be linked with variations in the apolipoprotein B gene, hypertension may be due to genetic variations in sodium or other transport systems, aortic aneurysms may be linked to variations in α-haptoglobin and cholesterol ester transfer protein, and alcoholism may be related to variant forms of alcohol dehydrogenase and mitochondrial aldehyde dehydrogenase. Furthermore, an individual's response to medicaments may be affected by variations in drug modification systems such as cytochrome P450s, and susceptibility to particular infectious diseases may also be influenced by genetic status. Finally, the methods of the present invention can be applied to HLA analysis for identity testing.

In yet another embodiment, the specific DNA sequence comprises part of a foreign genetic sequence e.g. the genome of an invading microorganism. Non-limiting examples include bacteria and their phages, viruses, fungi, protozoa, and the like. The present methods are particularly applicable when it is desired to distinguish between different variants or strains of a microorganism in order to choose appropriate therapeutic interventions.

The methods of the present invention encompass the steps of:

1) preparing heteroduplexes between patients' DNA and wild-type DNA;
2) cleaving mismatches to form a single-stranded gap across the site of the mismatch and;
3) determining the precise sequence that is altered, i.e. across the gap. These steps are described in detail below.

1. PREPARATION OF HETERODUPLEXES

In accordance with the present invention, the target DNA represents a sample of DNA isolated from an animal or human patient. This DNA may be obtained from any cell source or body fluid. Non-limiting examples of cell sources available in clinical practice include blood cells, buccal cells, cervicovaginal cells, epithelial cells from urine, fetal cells, or any cells present in tissue obtained by biopsy. Body fluids include blood, urine, cerebrospinal fluid, and tissue exudates at the site of infection or inflammation. DNA is extracted from the cell source or body fluid using any of the numerous methods that are standard in the art. It will be understood that the particular method used to extract DNA will depend on the nature of the source. The preferred amount of DNA to be extracted for analysis of human genomic DNA is at least 5 pg (corresponding to about 1 cell equivalent of a genome size of $4 \times 10^9$ base pairs). In some applications, such as, for example, detection of sequence alterations in the genome of a microorganism, variable amounts of DNA may be extracted.

Once extracted, the target DNA may be employed in the present invention without further manipulation. Preferably, one or more specific DNA regions present in the target DNA may be amplified by PCR. In this case, the amplified regions are specified by the choice of particular flanking sequences for use as primers. Amplification at this step provides the advantage of increasing the concentration of specific DNA sequences within the target DNA sequence population. The length of DNA sequence that can be amplified ranges from 80 bp to up to 30 kbp (Saiki et al., 1988, Science, 239:487). Furthermore, the use of amplification primers that are modified by, e.g., biotinylation, allows the selective incorporation of the modification into the amplified target DNA.

In one embodiment, the target DNA, with or without prior amplification of particular sequences, is bound to a solid-phase matrix. This allows the simultaneous processing and screening of a large number of patient samples. Non-limiting examples of matrices suitable for use in the present invention include nitrocellulose or nylon filters, glass beads, magnetic beads coated with agents for affinity capture, treated or untreated microtiter plates, and the like. It will be understood by a skilled practitioner that the method by which the target DNA is bound to the matrix will depend on the particular matrix used. For example, binding to nitrocellulose can be achieved by simple adsorption of DNA to the filter, followed by baking the filter at 75°–80° C. under vacuum for 15 min–2 h. Alternatively, charged nylon membranes can be used that do not require any further treatment of the bound DNA. Beads and microtiter plates that are coated with avidin can be used to bind target DNA that has had biotin attached (via e.g. the use of biotin-conjugated PCR primers.) In addition, antibodies can be used to attach target DNA to any of the above solid supports by coating the surfaces with the antibodies and incorporating an antibody-specific hapten into the target DNA. In a preferred embodiment, target DNA that has been amplified using biotinylated primers is bound to streptavidin-coated beads (Dynal, Inc., Milwaukee, Wis.).

In practicing the present invention, the untreated or amplified target DNA, preferably bound to a solid-phase matrix, is hybridized with a second DNA sample under conditions that favor the formation of mismatch loops. The second DNA sample preferably comprises one or more "wild-type" version(s) of the target DNA sequence. As used herein, a "wild-type" version of a gene is one prevalent in the general population that is not associated with disease (or with any discernable phenotype) and is thus carried by "normal" individuals. In the general population, wild-type genes may include multiple prevalent versions, which contain alterations in sequence relative to each other that cause no discernable pathological effect; these variations are designated "polymorphisms" or "allelic variants". Most preferably, a mixture of DNAs from "normal" individuals is used for the second DNA sample, thus providing a mixture of the most common polymorphisms. This insures that, statistically, hybrids formed between the first and second DNA sample will be perfectly matched except in the region of the mutation, where discrete mismatch regions will form. In some applications, it is desired to detect polymorphisms; in these cases, appropriate sources for the second DNA sample will be selected accordingly. Depending upon what method is used subsequently to detect mismatches, the wild-type DNA may also be chemically or enzymatically modified, e.g., to remove or add methyl groups.

Hybridization reactions according to the present invention are performed in solutions ranging from about 10 mM NaCl to about 600 mM NaCl, at temperatures ranging from about 37° C. to about 65° C. It will be understood that the stringency of a hybridization reaction is determined by both the salt concentration and the temperature; thus, a hybridization performed in 10 mM salt at 37° C. may be of similar stringency to one performed in 500 mM salt at 65° C. For the purposes of the present invention, any hybridization conditions may be used that form perfect hybrids between precisely complementary sequences and mismatch loops between non-complementary sequences in the same molecules. Preferably, hybridizations are performed in 600 mM NaCl at 65° C. Following the hybridization step, DNA molecules that have not hybridized to the target DNA sample are removed by washing under stringent conditions, e.g., 0.1X SSC at 65° C.

The hybrids formed by the hybridization reaction may then be treated to block any free ends so that they cannot serve as substrates for further enzymatic modification such as, e.g., by RNA ligase. Suitable blocking methods include without limitation removal of 5' phosphate groups, homopolymeric tailing of 3' ends with dideoxynucleotides, and ligation of modified double-stranded oligonucleotides to the ends of the duplex.

2. MISMATCH RECOGNITION AND CLEAVAGE

In the next step, the hybrids are treated so that one or both DNA strands are cleaved within, or in the vicinity of, the mismatch region. Depending on the method used for mismatch recognition and cleavage (see below), cleavage may occur at some predetermined distance from either boundary of the mismatch region, and may occur on the wild-type or mutant strand. The "vicinity" of the mismatch as used herein thus encompasses from 1 to 2000 bases from the borders of the mismatch. Non-limiting examples of mismatch recognition and cleavage systems suitable for use in the present invention include mismatch repair proteins, nucleotide excision repair proteins, chemical modification, and combinations thereof. These embodiments are described below.

In general, the mismatch recognition and/or modification proteins necessary for each embodiment described below are isolated using methods that are well known to those skilled in the art. Preferably, when the sequence of a protein is known, the protein-coding region of the relevant gene is isolated from the source organism by subjecting genomic DNA of the organism to PCR using appropriate primers. The isolated protein-coding DNA sequence is cloned into commercially available expression vectors that, e.g., insert an amino acid "purification tag" at either the amino- or carboxyterminus of the recombinant protein. The recombinant expression vector is then introduced into an appropriate host cell (e.g., E. coli), and the protein is recovered from the cell lysate by affinity chromatography that recognizes the "tag". For example, the bacterial expression vector pQiex12 is used to express proteins with a polyhistidine tag, allowing purification of the recombinant product by a single step of chromatography on Ni-Sepharose (QiaGen, Chatsworth, Calif.). Other methods involve the expression of recombinant proteins carrying glutathione-S-transferase sequences as tags, allowing purification of the recombinant products on glutathione affinity columns (Pharmacia Biotech, Uppsala, Sweden). If necessary, proteins containing purification tags are then treated so as to remove the tag sequences. Alternatively, the protein may be isolated from its cell of origin using standard protein purification techniques well-known in the art, including, e.g., molecular sieve, ion-exchange, and hydrophobic chromatography; and isoelectric focusing. "Isolation" as used herein denotes purification of the protein to the extent that it can carry out its function in the context of the present invention without interference from extraneous proteins or other contaminants derived from the source cells.

The mismatch recognition and modification proteins used in practicing the present invention may be derived from any species, from E. coli to humans, or mixtures thereof. Typically, functional homologues for a given protein exist across phylogeny. A "functional homologue" of a given protein as used herein is another protein that can functionally substitute for the first protein, either in vivo or in a cell-free reaction.

Mismatch repair proteins:

A number of different enzyme systems exist across phylogeny to repair mismatches that form during DNA replication. In *E. coli*, one system involves the MutY gene product, which recognizes A/G mismatches and cleaves the A-containing strand (Tsai-Wu et al., J. Bacteriol. 178:1902,1991). Another system in *E. coli* utilizes the coordinated action of the MutS, MutL, and MutH proteins to recognize errors in newly-synthesized DNA strands specifically by virtue of their transient state of undermethylation (prior to their being acted upon by dam methylase in the normal course of replication). Cleavage typically occurs at a hemimethylated GATC site within 1–2 kb of the mismatch, followed by exonucleolytic cleavage of the strand in either a 3'-5' or 5'-3' direction from the nick to the mismatch. In vivo, this is followed by re-synthesis involving DNA polymerase III holoenzyme and other factors (Cleaver, Cell, 76:1–4, 1994).

Mismatch repair proteins for use in the present invention may be derived from *E. coli* (as described above) or from any organism containing mismatch repair proteins with appropriate functional properties. Non-limiting examples of useful proteins include those derived from *Salmonella typhimurium* (MutS, MutL); *Streptococcus pneumoniae* (HexA, HexB); *Saccharomyces cerevisiae* ("all-type", MSH2, MLH1, MSH3); *Schizosaccharomyces pombe* (SWI4); mouse (rep1, rep3); and human ("all-type", hMSH2, hMLH1, hPMS1, hPMS2, duel). Preferably, the "all-type" mismatch repair system from human or yeast cells is used (Chang et al., Nuc. Acids Res. 19:4761, 1991; Yang et al., J. Biol. Chem. 266:6480,1991). In a preferred embodiment, heteroduplexes formed between patients' DNA and wild-type DNA as described above are incubated with human "all-type" mismatch repair activity that is purified essentially as described in International Patent Application WO/93/20233. Incubations are performed in, e.g., 10 mM Tris-HCl pH 7.6, 10 mM $ZnCl_2$, 1 mM dithiothreitol, 1 mM EDTA and 2.9% glycerol at 37° C. for 1–3 hours. In another embodiment, purified MutS, MutL, and MutH are used to cleave mismatch regions (Su et al., Proc. Natl. Acad. Sci. USA 83:5057,1986; Grulley et al., J. Biol. Chem. 264:1000, 1989).

Nucleotide excision repair proteins:

In *E. coli*, four proteins, designated UvrA, UvrB, UvrC, and UvrD, interact to repair nucleotides that are damaged by UV light or otherwise chemically modified (Sancar, Science 266: 1954, 1994), and also to repair mismatches (Huang et al., Proc. Natl. Acad. Sci. USA 91:12213, 1994). UvrA, an ATPase, makes an $A_2B_1$ complex with UvrB, binds to the site of the lesion, unwinds and kinks the DNA, and causes a conformational change in UvrB that allows it to bind tightly to the lesion site. UvrA then dissociates from the complex, allowing UvrC to bind. UvrB catalyzes an endonucleolytic cleavage at the fifth phosphodiester bond 3' from the lesion; UvrC then catalyzes a similar cleavage at the eighth phosphodiester bond 5' from the lesion. Finally, UvrD (helicase II) releases the excised oligomer. In vivo, DNA polymerase I displaces UvrB and fills in the excision gap, and the patch is ligated.

In one embodiment of the present invention, heteroduplexes formed between patients' DNA and wild-type DNA are treated with a mixture of UvrA, UvrB, UvrC, with or without UvrD. As described above, the proteins may be purified from wild-type *E. coli*, or from *E. coli* or other appropriate host cells containing recombinant genes encoding the proteins, and are formulated in compatible buffers and concentrations. The final product is a heteroduplex containing a single-stranded gap covering the site of the mismatch.

Excision repair proteins for use in the present invention may be derived from *E. coli* (as described above) or from any organism containing appropriate functional homologues. Non-limiting examples of useful homologues include those derived from *S. cerevisiae* (RAD1, 2, 3, 4, 10, 14, and 25) and humans (XPF, XPG, XPD, XPC, XPA, ERCC1, and XPB) (Sancar, Science 266:1954, 1994). When the human homologues are used, the excised patch comprises an oligonucleotide extending 5 nucleotides from the 3' end of the lesion and 24 nucleotides from the 5' end of the lesion. Aboussekhra et al. (Cell 80:859, 1995) disclose a reconstituted in vitro system for nucleotide excision repair using purified components derived from human cells.

Chemical Mismatch Recognition:

Heteroduplexes formed between patients' DNA and wild-type DNA according to the present invention may be chemically modified by treatment with osmium tetroxide (for mispaired thymidines) and hydroxylamine (for mispaired cytosines), using procedures that are well known in the art (see, e.g., Grompe, Nature Genetics 5:111, 1993; and Saleeba et al., Meth. Enzymol. 217:288, 1993). In one embodiment, the chemically modified DNA is contacted with excision repair proteins (as described above). The hydroxylamine- or osmium-modified bases are recognized as damaged bases in need of repair, one of the DNA strands is selectively cleaved, and the product is a gapped heteroduplex as above.

Resolvases:

Resolvases are enzymes that catalyze the resolution of branched DNA intermediates that form during recombination events (including Holliday structures, cruciforms, and loops) via recognition of bends, kinks, or DNA deviations (Youil et al., Proc. Natl. Acad. Sci. USA 92:87, 1995). For example, Endonuclease VII derived from bacteriophage T4 (T4E7) recognizes mismatch regions of from one to about 50 bases and produces double-stranded breaks within six nucleotides from the 3' border of the mismatch region. T4E7 may be isolated from, e.g., a recombinant *E. coli* that overexpresses gene 49 of T4 phage (Kosak et al., Eur. J. Biochem. 194:779, 1990). Another suitable resolvase for use in the present invention is Endonuclease I of bacteriophage T7 (T7E1), which can be isolated using a polyhistidine purification tag sequence (Mashal et al., Nature Genetics 9:177, 1995).

In a preferred embodiment, heteroduplexes formed between patients' DNA and wild-type DNA as described above are incubated in a 50 µl reaction with 100–3000 units of T4E7 for 1 hour at 37° C.

3. SEQUENCE DETERMINATION

In practicing the present invention, immobilized target DNA from a patient is hybridized to wild-type DNA to form mismatch regions and then treated with mismatch repair proteins, excision repair proteins, chemical modification and cleavage reagents, or combinations of such agents. This treatment introduces single-stranded breaks at predetermined locations on one or both sides of a mismatch region and causes the selective excision of s single-stranded fragment covering the mismatch region. The resulting structure is a gapped heteroduplex in which the gap may be from about 5 to about 2000 bases in length, depending on the mismatch recognition system used.

To determine the nucleotide sequence of the excised region (including the mismatch), the heteroduplexes are incubated with an appropriate DNA polymerase enzyme in the presence of dideoxynucleotides. Suitable enzymes for use in this step include without limitation DNA polymerase I, DNA polymerase III holoenzyme, T4 DNA polymerase, and T7 DNA polymerase. The only requirement is that the enzyme be capable of accurate DNA synthesis using the gapped heteroduplex as a substrate. The presence of dideoxynucleotides, as in a Sanger sequencing reaction, insures that a nested set of premature termination products will be produced, and that resolution of these products by, e.g., gel electrophoresis will display the DNA sequence across the gap.

In some circumstances, the sequence obtained using this method will correspond to the wild-type strand and not to the patient's DNA in which the mutation is sought. This result is easily accomodated by a second round of sequencing, with or without prior amplification of the relevant DNA region. In this case, the sequence of the mutation is determined using as a template the patient's unmodified DNA in conjunction with sequencing primers derived from the sequence determined in the first round.

High-Throughput Applications

The methods of the present invention are particularly suitable for high-throughput analysis of DNA, i.e., the rapid and simultaneous processing of DNA samples derived from a large number of patients. Furthermore, in contrast to other methods for de novo mutation detection, the methods of the present invention are suitable for the simultaneous analysis of a large number of genetic loci in a single reaction; this is designated "multiplex" analysis. Therefore, for any one sample or for a multiplicity of samples, the present invention allows the analysis of both intragenic loci (several regions within a single gene) and intergenic loci (several regions within different genes) in a single reaction mixture. The manipulations involved in practicing the methods of the present invention lend themselves to automation, e.g., using multiwell microtiter dishes as a solid support or as a receptacle for, e.g., beads; robotics to perform sequential incubations and washes; and, finally, automated sequencing using commercially available automated DNA sequencers. It is contemplated that, in a clinical context, 500 patient DNA samples can be analyzed within 1–2 days in a cost-effective manner (less than $50.00/sample).

Positional Cloning

The methods of the present invention are also suitable for positional cloning of unknown genes that cause pathological conditions or other detectable phenotypes in any organism. "Positional cloning" as used herein denotes a process by which a previously unknown disease-causing gene is localized and identified. For example, identification of multiplex families in which several members exhibit signs of a genetically-based syndrome often occurs even when the particular gene responsible for the syndrome has not been identified. Typically, the search for the unknown gene involves one or more of the following time- and labor-intensive steps: 1) cytogenetic localization of the gene to a relatively large segment of a particular chromosome; 2) assembly of overlapping cosmid or P1 clones that collectively cover several hundred thousand nucleotides corresponding to the identified chromosomal region; 3) sequencing the clones; and 4) transcript mapping to identify expressed protein-encoding regions of the gene.

The present invention offers an alternative, cost-effective method for localizing a disease-causing gene. Briefly, DNA from affected individuals is hybridized with normal DNA as described above to form mismatch regions at the site of the mutation. Preferably, large regions of DNA corresponding to the chromosomal location are amplified from the patient's genomic DNA prior to inclusion in the hybridization reaction. The hybrids are then treated by any of the methods described above so that mismatch regions are recognized and cleaved, forming gapped heteroduplexes across the mismatch region. Finally, the sequence in the vicinity of the mismatch region is determined.

In this embodiment, determination of even a short sequence in the vicinity of the mismatch facilitates definitive identification of the disease-causing gene. The short sequence that is determined in the first round of sequencing can be used to design oligonucleotide probes for use in screening genomic or cDNA libraries. Other methods in which the primary sequence information can be used, either alone or in conjunction with library screening, include identification of tissue specific expression, reverse transcription-PCR amplification of mRNA, and screening of an affected population for genotype/phenotype association. Thus, without wishing to be bound by theory, it is contemplated that a previously unknown gene that causes a disease or other phenotype can be quickly and efficiently identified by these methods.

The following examples are intended to illustrate the present invention without limitation.

EXAMPLE 1

Preparation of Target DNA

A) Preparation of Sample DNA from Blood

Whole blood samples collected in high glucose ACD VacutainersTM (yellow top) were centrifuged and the buffy coat collected. The white cells were lysed with two washes of a 10:1 (v/v) mixture of 14 mM $NH_4Cl$ and 1 mM $NaHCO_3$, their nuclei were resuspended in nuclei-lysis buffer (10 mM Tris, pH 8.0, 0.4M NaCl, 2 mM EDTA, 0.5% SDS, 500 ug/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA.)

B) Preparation of Sample DNA from Buccal Cells

Buccal cells were collected on a sterile cytology brush (Scientific Products) or female dacron swab (Medical Packaging Corp. ) by twirling the brush or swab on the inner cheek for 30 seconds. DNA was prepared as follows, immediately or after storage at room temperature or at 4° C. The brush or swab was immersed in 600 µl of 50 mM NaOH contained in a polypropylene microcentrifuge tube and vortexed. The tube, still containing the brush or swab, was heated at 95° C. for 5 min, after which the brush or swab was carefully removed. The solution containing DNA was then neutralized with 60 µl of 1M Tris, pH 8.0, and vortexed again (Mayall et al., J. Med. Genet. 27:658, 1990). The DNA was stored at 4° C.

C) Amplification of Target DNA Prior to Hybridization

DNA from patients with CF was amplified by PCR in a Perkin-Elmer Cetus 9600 Thermocycler. Five primer sets were used to simultaneously amplify relevant regions of exons 4, 10, 20, and 21 of the cystic fibrosis transmembrane conductance regulator (CFTR) gene (Richards et al., Human Mol. Gen. 2:159, 1993). The 50 µl PCR reaction mix contained the following components: 0.2–1 µg CF patient DNA, 10 mM Tris pH 8.3, 50 mM KCl, 1.5 mM MgCl2, 0.01% (w/v) gelatin, 200 µM of each deoxynucleotide triphosphate, 0.4 µM of each amplification primer, and 2.5 units of Taq polymerase. An initial denaturation was performed by incubation at 94° C. for 20 seconds, followed by 28 cycles of amplification, each consisting of 10 seconds at 94° C., 10 seconds at 55° C., 10 seconds at 74° C., and a final soak at 74° C. for 5 min. Following amplification, 8 μl of the PCR products were electrophoresed in a 2% agarose gel to verify the presence of all five products.

D) Binding of DNA to a Solid Matrix:

For binding of amplified DNA to a solid support, the amplification reactions described above are performed in the present of biotinylated primers. The biotinylated products are then incubated with Dynabeads® M-280 Streptavidin (Dynal) in a solution containing 10 mM Tris HCl, pH 7.5, 1 mM EDTA, 2M NaCl, and 0.1% Tween-20 for 15–30 minutes at 48° C.

EXAMPLE 2

Hybridization of target DNA and wild-type DNA

A) Preparation of wild-type DNA:

DNA is prepared from blood or buccal cells of healthy individuals as described in Example 1. A representative "wild-type" DNA sample is prepared by combining and thoroughly mixing DNA samples derived from 10–200 individuals.

B) Hybridization Reaction:

Hybridizations are carried out in microtiter dishes containing bead-immobilized DNA prepared as in Example 1D above. The hybridization solution contains approximately 500 μg/ml wild-type DNA (prepared as in Example 2A above) and approximately 50 μg/ml amplified immobilized target DNA (prepared as in Example 1) in 10 mM Tris HCl pH 7.5–650 mM NaCl. The reaction mixtures are heated at 90° C. for 3 minutes, after which hybridizations are allowed to proceed for 1 hour at 65° C. The hybridization solution is then removed and the beads are washed three times in 0.1×SSC at 65° C.

C) Blocking of free ends:

The beads containing DNA:DNA hybrids prepared as described above are treated so that free ends become blocked and no longer accessible to modification by, e.g., RNA ligase. The wells are incubated in 100 μl of a solution containing 0.4M potassium cacodylate, 50 mM Tris HCl, pH 6.9, 4 mM dithiothreitol, 1 mM $CoCl_2$, 2 mM ddGTP, 500 μg/ml bovine serum albumin, and 2 units of terminal transferase for 15 minutes at 37° C.

EXAMPLE 3

Mismatch Recognition, Cleavage, and Sequencing

Four identical reactions mixtures, each containing 50 ul beads to which DNA hybrids prepared as described in Example 2 are bound, are incubated with 2 μl of a 10X T4 Polymerase buffer (50 mM NaCl, 10 mM Tris-HCl, pH 7.9, 10 mM $MgCl_2$, 1 mM dithiothreitol, and 1 mg/ml bovine serum albumin); 16 μl water; 1 μl T4 endonuclease 7 (250–3000 units, obtained as described in Kosak et al., Eur. J. Biochem. 19.4:779, 1990); and 1 μl T7 DNA polymerase (3 units). The reaction is allowed to proceed for 1–10 minutes at 37° C.

9 μl of a "termination mix" is then added to each reaction. "Termination mix" contains 8 μM of a single ddNTP (i.e., ddGTP, ddATP, ddTTP, or ddCTP) and 80 μM of all four dNTPs, one of which is labelled with a radioactive or fluorescent label. In addition, 1 μl of 10X T4 polymerase buffer is added, and the reaction is allowed to proceed for 5 minutes at 37° C.

The reaction mix is removed and the beads are washed three times with 100 μl TE (10 mM Tris-HCl, pH 7.5, 1 mM EDTA). Finally, the beads are resuspended in 6 μl gel loading buffer (95% formamide, 20 mM EDTA, 0.05 % bromphenol blue, 0.05 % Xylene Cyanol FF). The buffer is removed from the beads and loaded on a 6% denaturing polyacrylamide DNA sequencing gel.

EXAMPLE 4

Mismatch Recognition and Cleavage using Chemical Mismatch Cleavage

Microtiter wells prepared as described in Examples 1 and 2 above are treated sequentially with hydroxylamine and osmium tetroxide.

A) Hyroxylamine treatment:

Hydroxylamine (obtained from Aldrich, Milwaukee, Wis.) is dissolved in distilled water, and the pH is adjusted to 6.0 with diethylamine (Aldrich) so that the final concentration is about 2.5M. 200 ul of the solution are incubated within the wells at 37° C. for 2 hours. The reaction is stopped by replacing the hydroxylamine solution with an ice-cold solution containing 0.3M sodium acetate, 0.1 mM EDTA, pH5.2, and 25 μg/ml yeast tRNA (Sigma, St. Louis, Mo.). The wells are then washed in an ice-cold solution of 10 mM Tris-HCl, pH 7.7, 1 mM EDTA prior to osmium tetroxide treatment.

B) Osmium tetroxide treatment:

Osmium tetroxide (Aldrich) is dissolved in 10 mM Tris-HCl, pH 7.7, 1 mM EDTA, and 1.5% (v/v) pyridine to a concentration of 4% (w/v). The wells are incubated with this solution for 2 hours at 37° C. The reaction is stopped by replacing the osmium tetroxide solution with an ice-cold solution containing 0.3M sodium acetate, 0.1 mM EDTA, pH5.2, and 25 μg/ml yeast tRNA.

EXAMPLE 5

Positional Cloning of a Disease-Causing Gene

The experiments described below are performed to rapidly localize and sequence a genomic region corresponding to a disease-causing gene.

A multiplex family in which a genetic disease is expressed is identified using standard clinical indicators. DNA samples are obtained from affected and unaffected individuals as described in Example 1 above; if by patterns of transmission the disease appears to be an autosomal recessive syndrome, DNA samples are obtained from those individuals presumptively heterozygous for the disease gene.

All DNA samples are subjected to mismatch analysis by hybridization to wild-type DNA as described in Example 2 above. The hybrids are then treated with mismatch repair proteins to form a gapped heteroduplex, and the sequence across the gap is determined as described in Example 3 above.

The sequences obtained from unaffected, affected, and presumptively heterozygous family members are compared with each other and with available sequence databases, using, for example, Sequencher (Gene Codes, Ann Arbor, Mich.) and Assembly Lign (Kodak, New Haven, Conn.) The sequences are also serve as the basis for design of oligonucleotide probes, which are chemically synthesized and used to probe human genomic DNA libraries.

What is claimed is:

1. A method for identifying one or more genetic alterations in a target sequence present in a first genomic DNA sample, which comprises:
   a) hybridizing said DNA sample with a second DNA sample, wherein said second sample does not contain the alteration(s), to form heteroduplex DNA containing a mismatch region at the site of an alteration(s);
   b) cleaving one strand of said heteroduplex in the target sequence to form a single-stranded gap across the site of said alteration(s);
   c) treating said cleaved heteroduplex with a DNA polymerase in the presence of dideoxynucleotides to determine the nucleotide sequence across said gap; and
   d) comparing said nucleotide sequence with a predetermined cognate wild-type sequence to identify said genetic alteration(s).

2. The method of claim 1, wherein the alterations are selected from the group consisting of additions, deletions, and substitutions of one or more nucleotides and combinations thereof.

3. The method of claim 1, wherein said target sequence is amplified prior to the hybridizing step.

4. The method of claim 3, wherein the first DNA sample is immobilized on a solid support prior to the hybridizing step.

5. The method of claim 4, wherein the solid support is selected from the group consisting of nitrocellulose filter, nylon filter, glass beads, and plastic.

6. The method of claim 1, wherein said cleaving step comprises exposing said heteroduplex DNA to one or more resolvase proteins under conditions appropriate for mismatch recognition and cleavage.

7. The method of claim 6, wherein the resolvases are selected from the group consisting of T4 endonuclease 7 and T7 endonuclease 1.

8. The method of claim 1, wherein said DNA polymerase is selected from the group consisting of DNA polymerase I, DNA polymerase III, T7 DNA polymerase, and T4 DNA polymerase.

9. The method of claim 1, wherein said cleaving step comprises exposing said heteroduplex DNA to one or more mismatch repair proteins under conditions appropriate for mismatch recognition, cleavage, and excision.

10. The method of claim wherein the one or more mismatch repair proteins comprise *Escherichia coli* proteins MutS, MutL, MutH, and MutU, or functional homologues thereof.

11. The method of claim 10, wherein the functional homologues are derived from species selected from the group consisting of *Salmonella typhimurium, Streptococcus pneumoniae, Saccharomyces cerevisiae, Schizosaccharomyces pombe,* mouse and human.

12. The method of claim 1, wherein said cleaving step comprises exposing said heteroduplex DNA to a mixture of nucleotide repair proteins under conditions appropriate for mismatch recognition, cleavage, and excision.

13. The method of claim 12, wherein the mixture comprises *E. coli* proteins UvrA, UvrB, UvrC, and UvrD, or functional homologues thereof.

14. The method of claim 13, wherein the functional homologues are derived from species selected from the group consisting of *Saccharomyces cerevisiae* and human.

15. The method of claim 1, further comprising determining the complement of said nucleotide sequence using said first DNA as a template.

16. A method for identifying one or more genetic alterations in a target sequence present in a first genomic DNA sample, which comprises:
   a) hybridizing the first DNA sample with a second DNA sample, wherein said second sample does not contain the alteration(s), to form heteroduplex DNA containing a mismatch region at the site of an alteration(s);
   b) treating said heteroduplex DNA with a mixture of T4 endonuclease 7 and DNA polymerase I in the presence of dideoxynucleotides to form premature termination products;
   c) resolving said termination products to determine the nucleotide sequence in the vicinity of the mismatch region; and
   d) comparing said nucleotide sequence with a predetermined cognate wild-type sequence to identify said alteration(s).

17. A method for multiplex identification of one or more mutation(s) in a DNA sample suspected of containing one or more mutations, the method comprising:
   a) immobilizing one or more DNA samples on a solid support;
   b) hybridizing said immobilized sample(s) with a second DNA sample, wherein said second sample does not contain the mutation(s), to form heteroduplex DNA containing a mismatch region at the site of a mutation(s);
   c) cleaving one or both strands of said heteroduplex adjacent to said mismatch region to form a gap at the site of said mutation(s);
   d) treating said cleaved heteroduplex with a DNA polymerase in the presence of dideoxynucleotides to determine the nucleotide sequence across said gap using enzymatic DNA sequencing; and
   e) comparing said nucleotide sequences with one or more predetermined cognate wild-type sequences to identify said mutation(s).

18. The method of claim 1 wherein the DNA samples are denatured prior to hybridization.

19. The method of claim 17 wherein the DNA samples are denatured prior to hybridization.

20. A method for identifying one or more genetic alterations in a target sequence present in a genomic DNA sample, which comprises:
   a) denaturing said DNA;
   b) reannealing said DNA to form heteroduplex DNA containing a mismatch region at the site of an alteration(s);
   c) cleaving one strand of said heteroduplex in said target sequence to form a single-stranded gap across the site of said alteration(s);
   d) treating said cleaved heteroduplex with a DNA polymerase in the presence of dideoxynucleotides to determine the nucleotide sequence across said gap; and
   e) comparing said nucleotide sequence with a predetermined cognate wild-type sequence to identify said alteration(s).

21. A method for positional cloning of a gene of interest, the method comprising:
   a) hybridizing a first DNA sample derived from an individual displaying a given phenotype with a second DNA sample, wherein said second DNA sample is derived from one or more individual(s) not displaying said phenotype, to form heteroduplex DNA containing a mismatch region at the site of an alteration(s);
   b) cleaving one strand of said heteroduplex DNA to form a single-stranded gap across said mismatch region;

c) treating said cleaved heteroduplex with a DNA polymerase in the presence of dideoxynucleotides to determine the nucleotide sequence across said gap;

d) preparing a synthetic oligonucleotide comprising all or part of said nucleotide sequence; and e) identifying a DNA clone that hybridizes to said oligonucleotide.

22. The method of claim 21, wherein the alteration(s) is selected from the group consisting of additions, deletions, and substitutions of one or more nucleotides and combinations thereof.

23. The method of claim 21, wherein said first DNA sample is immobilized on a solid support prior to the hybridizing step.

24. The method of claim 21, wherein said cleaving step comprises exposing said heteroduplex DNA to a mixture of mismatch repair proteins under conditions appropriate for mismatch recognition, cleavage, and excision.

25. The method of claim 24, wherein said mixture comprises *Escherichia coli* proteins MutS, MutL, MutH, and MutU, or functional homologues thereof.

26. The method of claim 25, wherein said functional homologues are derived from species selected from the group consisting of *Salmonella typhimurium, Streptococcus pneumoniae, Saccharomyces cerevisiae, Schizosaccharomyces pombe,* mouse and human.

27. The method of claim 21, wherein said cleaving step comprises exposing said heteroduplex DNA to a mixture of nucleotide excision repair proteins under conditions appropriate for mismatch recognition, cleavage, and excision.

28. The method of claim 27, wherein said mixture comprises *Escherichia coli* proteins, UvrA, UvrB, UvrC, and UvrD, or functional homologues thereof.

29. The method of claim 28, wherein said functional homologues are derived from species selected from the group consisting of *Saccharomyces cerevisiae* and human.

30. The method of claim 21, wherein said cleaving step comprises exposing said heteroduplex DNA to one or more resolvase proteins under conditions appropriate for mismatch recognition and cleavage.

31. The method of claim 30, wherein said resolvase protein(s) is selected from the group consisting of T4 endonuclease 7 and T7 endonuclease 1.

32. The method of claim 21, wherein said determining step comprises enzymatic DNA sequencing.

\* \* \* \* \*